US012725010B2

(12) United States Patent
Nehzati

(10) Patent No.: US 12,725,010 B2
(45) Date of Patent: Sep. 1, 2026

(54) OPTIMIZATION OF DEEP LEARNING ALGORITHMS FOR LARGE DIGITAL DATA PROCESSING USING EVOLUTIONARY NEURAL NETWORKS

(71) Applicant: VMC MAR COM Inc., Knoxville, TN (US)

(72) Inventor: Mohammadreza Nehzati, Berlin (DE)

(73) Assignee: VMC MAR COM INC., Knoxville, TN (US)

( * ) Notice: Subject to any disclaimer, the term of this patent is extended or adjusted under 35 U.S.C. 154(b) by 0 days.

(21) Appl. No.: 19/181,522

(22) Filed: Apr. 17, 2025

(65) Prior Publication Data

US 2026/0030487 A1 Jan. 29, 2026

Related U.S. Application Data

(60) Provisional application No. 63/675,138, filed on Jul. 24, 2024.

(51) Int. Cl.
*G06N 3/0464* (2023.01)
*G06N 3/044* (2023.01)
*G16H 50/20* (2018.01)

(52) U.S. Cl.
CPC ........... *G06N 3/0464* (2023.01); *G06N 3/044* (2023.01); *G16H 50/20* (2018.01)

(58) Field of Classification Search
CPC ....... G06N 3/0464; G06N 3/044; G16H 50/20
See application file for complete search history.

(56) References Cited

U.S. PATENT DOCUMENTS 9,264,483 B2 2/2016 Hammond
10,015,064 B2 7/2018 Li et al.
10,657,447 B1 * 5/2020 McDonnell ............ G06N 3/082
2019/0180186 A1 * 6/2019 Liang ................... G06N 3/0464
2020/0380339 A1 12/2020 Branson et al.
2021/0209512 A1 * 7/2021 Gaddam ............. H04L 63/1408
2023/0290502 A1 * 9/2023 Zhi ........................ G06N 3/044

FOREIGN PATENT DOCUMENTS

WO 2023/114519 A1 6/2023

OTHER PUBLICATIONS

Kostrzewa, Daniel, Michal Ciszynski, and Robert Brzeski. "Evolvable hybrid ensembles for musical genre classification." Proceedings of the Genetic and Evolutionary Computation Conference Companion. 2022. (Year: 2022).*

(Continued)

*Primary Examiner* — Miranda M Huang
*Assistant Examiner* — Sidney Vincent Bostwick
(74) *Attorney, Agent, or Firm* — Pillsbury Winthrop Shaw Pittman LLP

(57) ABSTRACT

Embodiments of the present disclosure relate to neural networks for processing large digital datasets. Neural networks comprise both a convolutional neural network (CNN) and a recurrent neural network (RNN). The neural networks are optimized by applying genetic algorithms. Embedding vectors are processed by both the CNN and the RNN to produce a merged output.

10 Claims, 6 Drawing Sheets

(56) References Cited

OTHER PUBLICATIONS

Chiba, Zouhair, et al. "Automatic building of a powerful IDS for the cloud based on deep neural network by using a novel combination of simulated annealing algorithm and improved self-adaptive genetic algorithm." International Journal of Communication Networks and Information Security 14.1 (Year: 2022).*

Choi, Keunwoo, et al. "Convolutional recurrent neural networks for music classification." 2017 IEEE International conference on acoustics, speech and signal processing (ICASSP). IEEE, 2017. (Year: 2017).*

Hao, Yixue, et al. "Recurrent convolutional neural network based multimodal disease risk prediction." Future Generation Computer Systems 92 (2019): 76-83. (Year: 2019).*

Gong, Jingtao, and Benjawan Srisura. "Heart Sound Detection Based on Bidirectional Multilayer Recurrent Convolutional Neural Network." Proceedings of the 2022 4th International Conference on Software Engineering and Development. 2022. (Year: 2022).*

Xue, Ning, et al. "Evolving deep CNN-LSTMs for inventory time series prediction." 2019 IEEE Congress on Evolutionary Computation (CEC). IEEE, 2019. (Year: 2019).*

Yilmaz, Doga, et al. "Image Classification Using CNN-LSTM Hybrid Model With Skip Connections." (Year: 2022).*

Fu, Yingwei, et al. "Multi model-based distillation for sound event detection." IEICE Transactions on Information and Systems 102.10 (2019): 2055-2058. (Year: 2019).*

Deshpande, Pallavi, et al. "Alzheimer disease progression forecasting: Empowering models through hybrid of cnn and lstm with pso op-timization." 2024 International Conference on Emerging Smart Computing and Informatics (ESCI). IEEE, 2024. (Year: 2024).*

Saleh, Hager, et al. "Genetic algorithm-based hybrid deep learning model for explainable Alzheimer's disease prediction using temporal multimodal cognitive data." International Journal of Data Science and Analytics 20.2 (2025): 1073-1103. (Year: 2025).*

Baniasadi et al., "Power Quality Disturbances Classification Using Identity Feature Vector and Support Vector Machine", Journal of Soft Computing and Information Technology, 2020, pp. 151-164, vol. 9(2), English Abstract.

Bhumika, P.S.S.S. et al., "A Review Paper on Algorithms Used for Text Classification", International Journal of Application or Innovation in Engineering & Management, Mar. 2013, pp. 90-99, vol. 3(2).

Chen, C. et al., "Mitigating Backdoor Attacks in LSTM-Based Text Classification Systems by Backdoor Keyword Identification", Neurocomputing, Mar. 15, 2021, pp. 1-13, vol. 452. 253-262.

Chen, Y.H. et al., "A hybrid text classification method based on K-congener-nearest-neighbors and hypersphere support vector machine", 2013 International Conference on Information Technology and Applications, IEEE, Nov. 2013, pp. 493-497.

Chen, J. et al., "Feature selection for text classification with Naïve Bayes", Expert Systems with Applications, 2009, pp. 5432-5435, vol. 36.

Padurariu et al., "Dealing with Data Imbalance in Text Classification", 23rd International Conference on Knowledge-Based and Intelligent Information & Engineering Systems, Procedia Computer Science, 2019, pp. 736-745, vol. 159.

Fang et al., "Automated text classification", Advanced Engineering Informatics, Mar. 2, 2020, pp. 1-8, vol. 44.

Goel et al., "A Novel Feature Selection and Extraction Technique for Classification", 14th International Conference on Frontiers in Handwriting Recognition, IEEE, 2014, pp. 104-109.

Golestanifar, et al., "Determination of Mental States from Texts Using Evolutionary Imperialist Competitive Algorithm and Convolution Neural Networks", Journal of Soft Computing and Information Technology, 2021, pp. 13-23, vol. 10(1), English Abstract.

Jang et al., "Sequential targeting: A continual learning approach for data imbalance in text classification", Expert Systems With Applications, Apr. 21, 2021, pp. 1-9, vol. 179.

Kim et al., "Some Effective Techniques for Naive Bayes Text Classification", IEEE Transactions on Knowledge and Data Engineering, Nov. 2006, pp. 1457-1466, vol. 18(11).

Li, Y., et al., "Imbalanced text sentiment classification using universal and domain-specific knowledge", Knowledge-Based Systems, Jul. 2018, pp. 1-15, vol. 160.

Li, Z., et al., "End-to-End Adversarial Memory Network for Cross-domain Sentiment Classification", Proceedings of the Twenty-Sixth International Joint Conference on Artificial Intelligence (IJCAI-17), Aug. 2017, pp. 2237-2243.

Luo et al., "Efficient English text classification using selected Machine Learning Techniques", Alexandria Engineering Journal, Feb. 21, 2021, pp. 3401-3409, vol. 60.

Pop, I., "An approach of the Naive Bayes classifier for the document classification", General Mathematics, 2006, pp. 135-138, vol. 14(4).

Singh et al., "Analysis of Vector Space Model in Information Retrieval", Proceedings published by International Journal of Computer Applications, 2012, pp. 14-18.

Sun et al., "On strategies for imbalanced text classifification using SVM: A comparative study", Decision Support Systems, 2009, pp. 191-201, vol. 48(1).

Tarekegn et al., "A review of methods for imbalance d multi-lab el classification", Pattern Recognition, 2021, pp. 1-12, vol. 118.

Thabtah et al., "Data imbalance in classification: Experimental evaluation" Information Sciences, 2020, pp. 429-441, vol. 513.

Ting et al., "Is Naïve Bayes a Good Classifier for Document Classification?", International Journal of Software Engineering and Its Applications, 2011, pp. 37-46, vol. 5(3).

Tsatsaronis et al., "A Generalized Vector Space Model for Text Retrieval Based on Semantic Relatedness", Proceedings of the EACL 2009 Student Research Workshop, Apr. 2, 2009, pp. 70-78.

Xiao et al., "History-based attention in Seq2Seq model for multi-label text classification", Knowledge-Based Systems, 2021, pp. 1-11, vol. 224.

Goldberg, "Genetic Algorithms in Search, Optimization, and Machine Learning", Jan. 1989, Addison-Wesley Publishing Company, Inc., Cover, Forward, Preface, Contents, pp. 1-130.

Goldberg, "Genetic Algorithms in Search, Optimization, and Machine Learning", Jan. 1989, Addison-Wesley Publishing Company, Inc., pp. 131-260.

Goldberg, "Genetic Algorithms in Search, Optimization, and Machine Learning", Jan. 1989, Addison-Wesley Publishing Company, Inc., pp. 261-412.

Schmidhuber, "Deep learning in neural networks: An overview", Neural Networks, 2015, pp. 85-114, vol. 61.

Xie et al., "Genetic CNN", 2017 IEEE International Conference on Computer Vision (ICCV), 2017, pp. 1379-1388.

Nehzati, "Optimization of deep learning algorithms for large digital data processing usingnetworks", Memories—Materials, Devices, Circuits and Systems, 2025, pp. 1-7.

European Patent Office; Extended European Search Report issued in corresponding EP 25187938.3, Nov. 26, 2025, pp. 1-9.

* cited by examiner

OPTIMIZATION OF DEEP LEARNING ALGORITHMS FOR LARGE DIGITAL DATA PROCESSING USING EVOLUTIONARY NEURAL NETWORKS

RELATED PATENT APPLICATIONS

This patent application claims the benefit of U.S. Provisional Patent Application No. 63/675,138 filed on Jul. 24, 2024. The entire content of the foregoing patent application is incorporated herein by reference, including all text, tables and drawings.

BACKGROUND

This disclosure generally relates to neural network architectures and methods of training neural networks.

Evolutionary neural networks are a class of machine learning techniques that employ evolutionary algorithms to optimize the structure and/or parameters of artificial neural networks. Unlike traditional training methods such as backpropagation, which adjust neural weights through gradient descent, evolutionary neural networks simulate the process of natural selection by generating a population of candidate networks, evaluating their performance on a specified task, and applying genetic operators—such as selection, crossover, and mutation—to produce successive generations of improved networks.

SUMMARY

Traditional optimization methods for deep learning algorithms, such as gradient-based techniques, often struggle to handle large-scale datasets. These methods may converge slowly, fail to reach a desired accuracy level, and/or struggle to sufficiently explore the vast search space of possible model parameters.

Embodiments of the present disclosure combine genetic evolutionary neural network approaches with a hybrid neural network architecture comprising a convolutional neural network (CNN) and recurrent neural network (RNN). CNNs excel in processing structured data, such as images, while RNNs are ideal for analysis of sequential data, including natural language. Embodiments of the present disclosure enhance neural networks' performance in processing large digital datasets by combining the two architectures and refining the combination using evolutionary algorithms.

Some embodiments initialize a first plurality of neural networks. Performance metrics are determined, each of the performance metrics corresponding to a respective neural network of the first plurality of neural networks. Each of the performance metrics is based on accuracy of the respective neural network in evaluating a training dataset. A subset of the first plurality of neural networks is selected based on the performance metrics. A first neural network and a second neural network are selected from the subset. The first neural network comprises a first CNN and a first RNN. The second neural network comprises a second CNN and a second RNN. A third neural network is formed. Forming the third neural network comprises selecting weights of the first neural network, selecting weights of the second neural network, and forming the third neural network at least in part from the selected weights of the first and second neural networks.

In some embodiments, the third neural network is formed at least in part from the selected weights of the first and second neural networks, including (a) forming a third CNN of the third neural network from weights of the first CNN and weights of the second CNN and (b) forming a third RNN of the third neural network from weights of the first RNN and weights of the second RNN.

In some embodiments, first and second subsets of embedding vectors are processed by the third CNN, producing first and second CNN outputs. The third RNN processes the second CNN output, producing an RNN output. The first CNN output is combined with the RNN output, thereby producing a merged output. Input data is classified based on the merged output.

In some embodiments, the first RNN comprises a first long short-term memory (LSTM) network, the second RNN comprises a second LSTM network, and the third RNN comprises a third LSTM network.

Some embodiments include a tangible, non-transitory, machine-readable memory storing instructions that, when executed by a data processing apparatus such as a processor, cause the data processing apparatus to perform one or more described operations.

Some embodiments include a system comprising one or more processors, memory, or other components. The memory stores instructions that, when executed by the one or more processors, effectuate one or more described operations.

BRIEF DESCRIPTION OF THE DRAWINGS

The above-mentioned aspects and other aspects of the present techniques will be better understood when the present application is read in view of the following figures in which like numbers indicate similar or identical elements.

DETAILED DESCRIPTION OF CERTAIN EMBODIMENTS

Figure 1A:
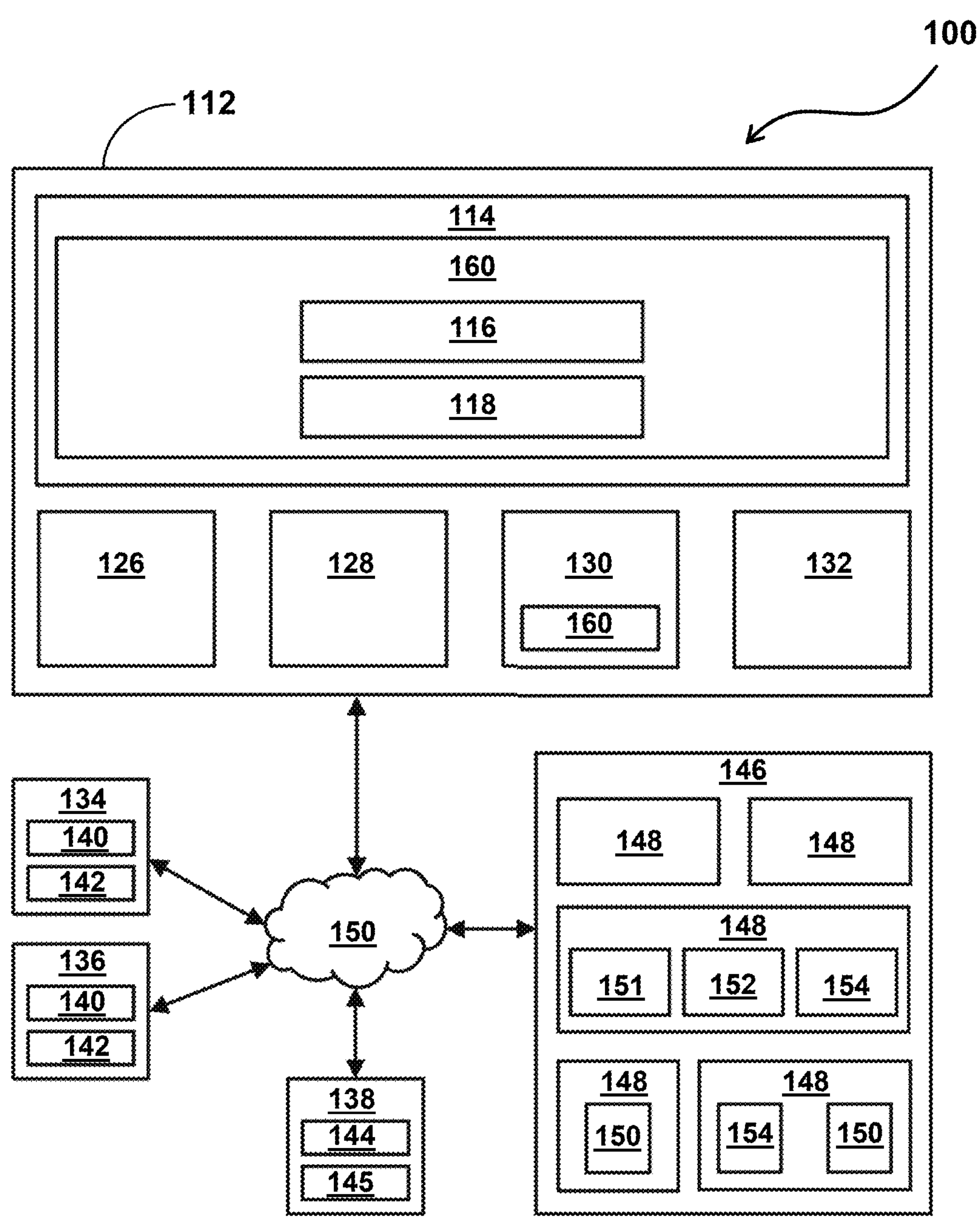
FIG. 1A is a logical-architecture block diagram that illustrates a system configured for training and inference via neural networks.

FIG. 1A illustrates a system 100 comprising a computing engine 112 and other components configured for neural network training and inference. In embodiments, the system 100 combines evolutionary algorithms with a hybrid neural network architecture, which improves both the efficiency of the training process and the classification accuracy of the resulting neural networks.

Prior optimization methods for deep learning algorithms, such as gradient-based techniques, often face challenges in handling large-scale datasets. These methods may converge slowly, find suboptimal solutions, and experience difficulties in exploring the vast search space of parameters.

Embodiments disclosed herein improve the computational efficiency and performance of deep learning algorithms when processing large-scale digital data. The embodiments' hybrid model architecture and iterative selection process enhance the accuracy, convergence speed, and generalization capabilities of deep learning models on extensive datasets.

Unlike prior approaches, embodiments of the present disclosure leverage a hybrid model architecture that includes both a CNN and an RNN, such as an LSTM. CNNs are typically ideal for processing grid-like data, such as images. RNNs (including LSTM networks) are best for analyzing time-sequence data, including natural language data. Embodiments of the present disclosure generate outputs from both a CNN and an RNN, and in doing so, draw on the benefits of both approaches.

These neural networks are particularly accurate at drawing inferences from multi-modal data, including EHRs. EHRs typically comprise data in many forms—e.g., images (x-rays, pictures, etc.), natural language information, and so on. Models disclosed herein, including those that merge outputs from a CNN and an RNN (e.g., an LSTM network), excel at processing such data (and other forms of data) due in part to the hybrid model architecture.

Training these models is far from a trivial task. Their unconventional structure makes optimization complex. Accordingly, and to achieve other benefits, embodiments of the present disclosure apply genetic algorithms to guide the model training process. As discussed, evolutionary neural networks simulate the process of natural selection by generating a population of candidate networks, evaluating their performance on a specified task, and applying genetic operators to produce successive generations of improved networks. Testing has shown that this approach successfully refines the neural networks of the varieties disclosed herein, delivering superior accuracy in a computationally efficient manner.

In these and other ways, system 100 provides technical solutions to technical problems related to training and using neural networks, including in the context of large datasets comprising multiple types of data. System 100 provides a new structure (e.g., hybrid neural network architectures) that facilitates efficient analysis of large datasets. System 100 also improves human-computer interaction, reduces the burden on a user to manually analyze data and/or tweak model parameters, and increases the computational efficiency of model training.

Returning to FIG. 1A, more details related to the technical solution(s) provided by system 100 are described below, after introducing the components of system 100 and describing their operation. It should be noted, however, that not all embodiments necessarily provide all of the benefits outlined herein, and some embodiments provide all or a subset of these benefits or different benefits, as various engineering and cost tradeoffs are envisioned, which is not to imply that other descriptions are limiting.

System 100 includes computing engine 112, mobile user devices 134 and 136, a desktop user device 138, and external resources 146. Interaction with users or other entities occurs via a website or a native application viewed on a desktop user device 138, a mobile user device 134 or 136, or other components. In some embodiments, interaction occurs via a desktop user device 138 such as a desktop computer, a mobile website viewed on a smart phone, tablet, or other mobile user device 134 or 136, or via a special-purpose native application executing on a smart phone, tablet, or other mobile user device.

In some embodiments, computing engine 112 includes one or more of a processor 114, an application program interface (API) server 126, a web server 128, a memory 130, and a cache server 132. These components, in some embodiments, communicate with one another in order to provide the functionality of computing engine 112 described herein.

To illustrate an example of the environment in which computing engine 112 operates, FIG. 1A includes a number of components with which computing engine 112 communicates: mobile user devices 134 and 136; a desktop user device 138; and external resources 146. Each of these devices communicates with computing engine 112 via a network 150, such as the Internet or the Internet in combination with various other networks, like local area networks, cellular networks, Wi-Fi networks, or personal area networks.

Mobile user devices 134 and 136 comprise smart phones, tablets, gaming devices, or other hand-held networked computing devices having a display, a user input device (e.g., buttons, keys, voice recognition, or a single or multi-touch touchscreen), memory (such as a tangible, machine-readable, non-transitory memory), a network interface, a portable energy source (e.g., a battery), and a processor (a term which, as used herein, includes one or more processors) coupled to each of these components. The memory of mobile user devices 134 and 136 stores instructions that when executed by the associated processor provide an operating system and various applications, including a web browser 142, a native mobile application 140, or both. The desktop user device 138 also includes a web browser 144, a native application 145, or other electronic resources. In addition, desktop user device 138 includes a monitor; a keyboard; a mouse; memory; a processor; and a tangible, non-transitory, machine-readable memory storing instructions that when executed by the processor provide an operating system and the web browser 144 or the native application 145.

Native applications 140 and 145, and web browsers 142 and 144, in some embodiments, are operative to provide a graphical user interface associated with a user, for example, which communicates with computing engine 112 and facilitates user interaction with data from computing engine 112. In some embodiments, computing engine 112 is stored on or otherwise executed by user computing resources (e.g., a user computer, server, etc., such as mobile user devices 134 and 136, and desktop user device 138 associated with a user), servers external to the user, or in other locations. In some embodiments, computing engine 112 is be run as an application (e.g., an app such as native application 140) on a server, a user computer, or other devices.

External resources 146 include sources of information such as databases, websites, etc.; external entities participating with system 100; one or more servers outside of system 100; a network (e.g., the internet); electronic storage; equipment related to Wi-Fi technology; equipment related to Bluetooth® technology; data entry devices; or other resources. External resources 146 include available data sources 148. Available data sources 148 may comprise a large and varying set of data sources, with many different characteristics. In some embodiments, available data sources 148 comprise databases 151 (which themselves comprise storage technologies of various types—e.g., tabular data, graph data, embedding vectors, etc.—the approach is not restricted to just tabular data, such as Kusto tables), data tables 152, columns of data 154, documents, charts, images, video, sensor data, or other data.

In some embodiments, available data sources 148 include electronic health records (EHRs). An EHR is a digital version of a patient's medical history, maintained by one or more healthcare providers, that includes comprehensive health information. EHR data may be derived from a medical doctor, orthodontist, dentist, and/or other medical provider. EHRs may comprise patient demographics, diagnoses, treatments, medications, allergies, laboratory results, test results, clinical notes, vitals, imaging/radiology reports, care plans, billing information, insurance information, appointment information, referral/specialist reports, and/or other relevant information.

Even though only a small number of available data sources 148 are shown in FIG. 1A, these are intended to represent tens, hundreds, thousands, millions, or billions of different available data sources 148. In some embodiments, some or all of the different available data sources 148 are co-located (e.g., in a database server associated with a user), or individual available data sources 148 are located remotely from other data sources 148 (e.g., in different database servers associated with an organization and located across the world).

In some embodiments, some or all of the functionality attributed to external resources 146 is provided by resources included in system 100. External resources 146 are configured to communicate with computing engine 112, mobile user devices 134 and 136, desktop user device 138, or other components of system 100 via wired or wireless connections, via network 150 (e.g., a local area network and/or the internet), via cellular technology, via Wi-Fi technology, or via other resources.

Thus, computing engine 112, in some embodiments, operates in the illustrated environment by communicating with a number of different devices and transmitting instructions to various devices to communicate with one another. The number of illustrated external resources 146, desktop user devices 138, and mobile user devices 136 and 134 is selected for explanatory purposes only, and embodiments are not limited to the specific number of any such devices illustrated by FIG. 1A, which is not to imply that other descriptions are limiting.

Memory 130 stores instructions 160 that, when executed by processor 114, cause processor 114 to execute the various operations described herein. In some embodiments, memory 130 stores or is configured to access other data required for training and/or inference, or other information that otherwise allows system 100 to function as described herein. In some embodiments, memory 130 includes various types of data stores, including relational or non-relational databases; image, document, etc., collections; or programming instructions related to storage and execution of a related multimodal model (large language models, generative models, etc.) for example. In some embodiments, such components are formed in a single database, or are stored in separate data structures. In some embodiments, memory 130 comprises electronic storage media that electronically stores information. In some embodiments, the electronic storage media of memory 130 includes one or both of system storage that is provided integrally (i.e., substantially non-removable) with system 100 or other storage that is connectable (wirelessly or via a wired connection) to system 100 via, for example, a port, a drive, a network (e.g., the Internet), etc. In some embodiments, memory 130 is (in whole or in part) a separate component within system 100, or memory 130 is provided (in whole or in part) integrally with one or more other components of system 100 (e.g., processor 114). In some embodiments, memory 130 is located in a data center, in a server that is part of external resources 146, in a computing device 134, 136, or 138, or in other locations. In some embodiments, memory 130 includes one or more of optically readable storage media, magnetically readable storage media, electrical charge-based storage media (e.g., EPROM, RAM, etc.), solid-state storage media, or other electronically readable storage media. In some embodiments, memory 130 stores software algorithms, information determined by processor 114, information received (e.g., a user input query or prompt) via a graphical user interface displayed on computing devices 134, 136, or 138, information received from external resources 146 (e.g., training data from an available data source 148), or other information accessed by system 100 to function as described herein.

Processor 114 is configured to coordinate the operation of the other components of computing engine 112 to provide the functionality described herein. In some embodiments, processor 114 is formed by two or more processors, for example. As shown in FIG. 1A, in some embodiments, instructions 160 comprise a training module 116 and an inference module 118. Processor 114 is configured to direct the operation of modules 116 and 118 by software; hardware; firmware; some combination of software, hardware, or firmware; machine-readable instructions; or other mechanisms for configuring processing capabilities.

Figure 2:
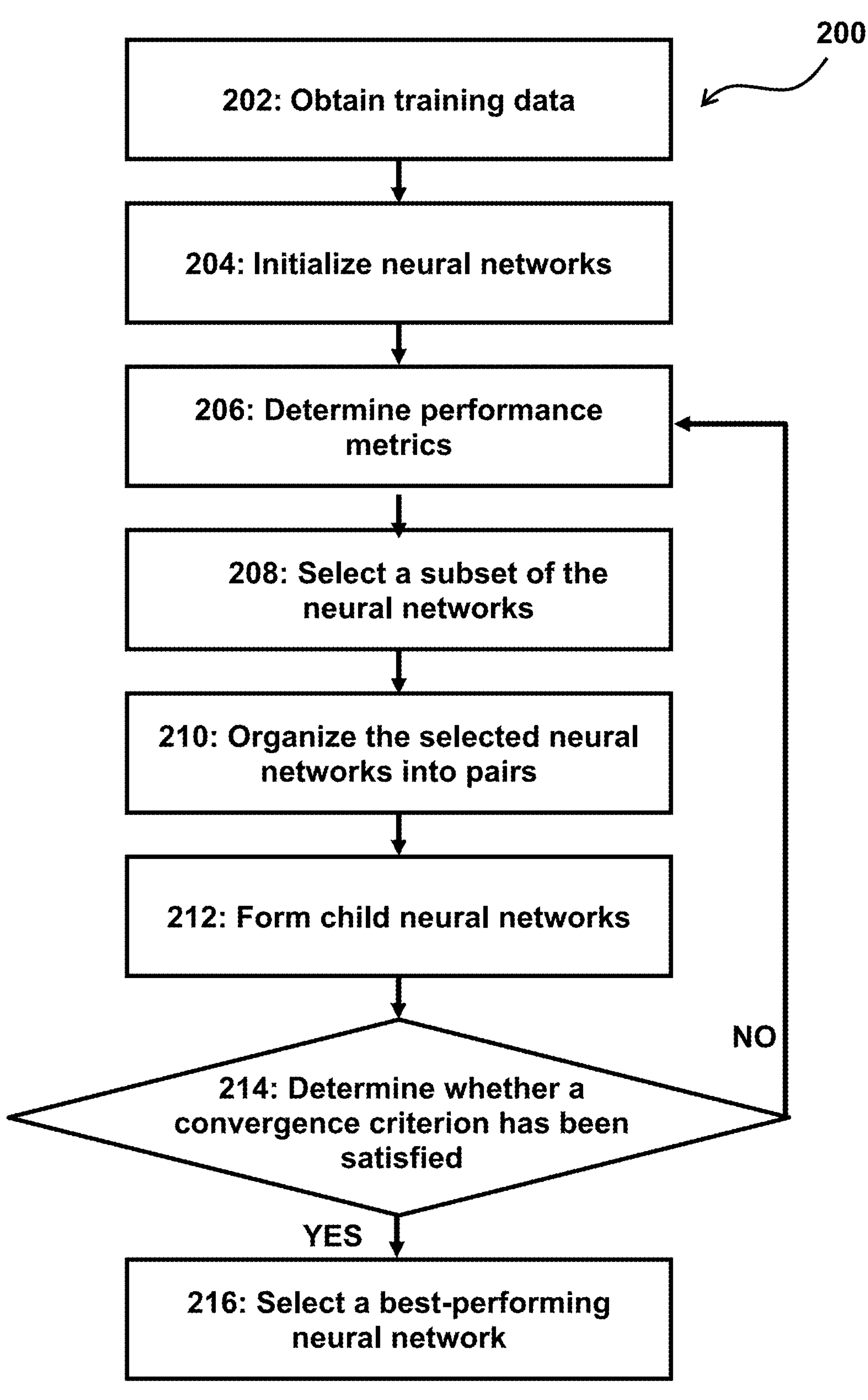
FIG. 2 illustrates an example method for training neural networks.

At a high level, training module 116 trains a plurality of neural networks. FIG. 2 illustrates an example training process 200. The training module may execute one or more of the steps in the training process 200.

At step 202, the training module 116 obtains training data. The training data may be obtained from data source 148. The training data may comprise any suitable form of data, such as natural language data, time-series data (such as sensor data, stock-price data, or weather data), audio data, video data, and/or medical data (e.g., EHRs). In some embodiments, the training module 116 generates additional, artificial training data. For example, in embodiments in which the training data comprises EHRs, the training module 116 may generate artificial EHRs by combining elements from patient EHRs (i.e., non-artificial EHRs). For instance, the training module 116 may create an artificial record comprising a first patient's name from a first EHR, a second patient's date of birth from a second EHR, a third patient's medical condition from a third EHR, and so on. This approach produces a robust training dataset from a comparatively small amount of training data.

In some embodiments, data maps (e.g., knowledge graphs) are formed of data in the available data sources 148—e.g., to improve training efficiency or debug model behavior. In such cases, the data map and/or underlying data may comprise a cyclical referential dependency. For example, a first node of the data map may point to a second node of the data map, which may in turn point back to the first node.

After identifying a cyclical referential dependency, the training module 116 may create a first preliminary placeholder entry for the first node and a second preliminary placeholder entry for the second node. Each preliminary placeholder entry may comprise partial data sufficient to establish initial referential integrity without requiring the complete existence of the other resource. The training module 116 may update the references within the first and second nodes such that each resource points to either the other's placeholder or the fully realized record. This may ensure consistency is preserved for all intermediate and final states. The first and second nodes may be updated accordingly. The update may occur within one atomic transaction, which may prevent partial failures or inconsistencies if one operation succeeds but another fails. Each placeholder entry may be converted into a fully populated record.

At step 204, the training module 116 initializes neural networks. In some embodiments, some or all of the initialized neural networks initially comprise random weights. In some embodiments, each of the neural networks comprises a convolutional neural network (CNN). The CNN may be a two-dimensional CNN.

In some embodiments, each of the neural networks comprises a recurrent neural network (RNN). In some embodiments, each RNN is a long short-term memory (LSTM) network. In some embodiments, each of the neural networks comprises both a CNN and an RNN (such as an LSTM network). RNNs are a class of neural networks designed for sequential data processing. In an RNN, information from previous time steps influences the current state. LSTM networks are a specialized type of RNN. They comprise a gating mechanism that includes input, output, and forget gates. They enhance traditional RNNs by mitigating memory loss over extended sequences, making them particularly useful for tasks such as speech recognition, time series forecasting, and natural language processing.

In one suitable embodiment, the LSTM network comprises a single LSTM layer with 256 hidden units followed by a fully connected layer with a softmax activation for classification. The LSTM network may comprise approximately two million parameters. The LSTM network's input may comprise a sequence length of about one hundred time steps, each with a feature size of about 300 embeddings.

Figure 3:
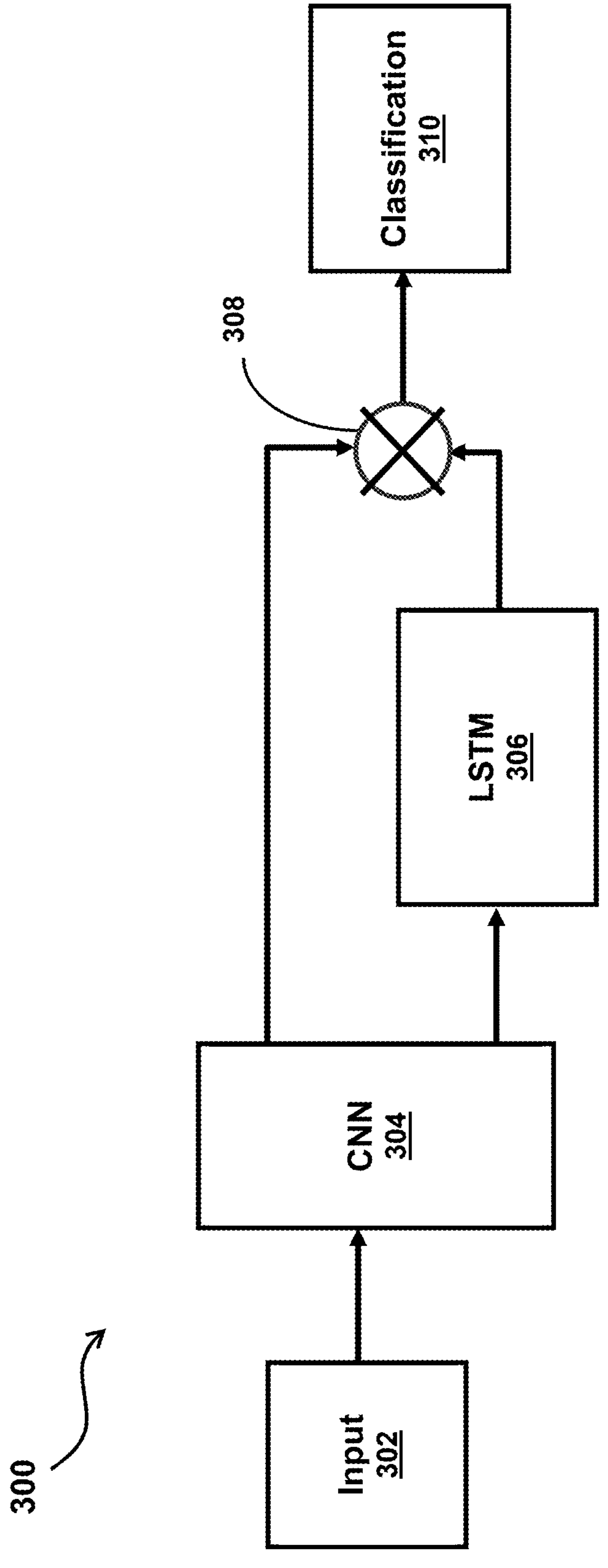
FIG. 3 illustrates an example inference process, including an example neural network architecture.

FIG. 3 includes, among other things, an illustration of an example architecture for the neural networks generated at step 204 of FIG. 2. As shown, in some embodiments, an input embedding is first processed by the CNN 304. A first portion of the CNN 304 produces a first output. A second portion of the CNN produces a second output that is provided to the LSTM network 306. The LSTM network 306 produces a third output that is merged (step 308) with the first output from the CNN and used to classify the input data. The process of merging the first and third outputs is discussed in more detail below.

Testing has shown that this hybrid CNN-LSTM architecture, particularly when combined with the evolutionary learning approach described below, significantly improves model performance compared to traditional architectures/approaches. Using CNNs to learn vector representations of expressions, applying these features to LSTMs, and merging CNN and LSTM outputs improves classification accuracy.

Returning to FIG. 2, at step 206, the training module 116 determines performance metrics for each of the initialized neural networks. Determining performance metrics at this stage allows weaker models to be weeded out, increasing efficiency, among other benefits. Each neural network's performance metric(s) may be based on the neural network's accuracy, speed of convergence, mean-squared error, generalization capability, and/or other factors. The inference-time process on which the performance metrics are based may be based on training data from the training dataset (e.g., training data may be used as input for inference) and may be performed by the inference module 118. The inference process is described in more detail below with respect to FIG. 3.

At step 208, the training module 116 selects a subset of the neural networks. One purpose of the selection may be to choose the neural networks that will be the "parents" for the following generation in the evolutionary process, as discussed in more detail below. In some embodiments, the training module 116 selects a predetermined number of the highest-performing neural networks—e.g., the neural networks with the best or highest performance metrics. In other embodiments, the training module 116 selects a predetermined number of the highest-performing neural networks but does so probabilistically. That is, in such embodiments, the training module 116 selects higher-performing neural networks with greater probability but does not necessarily select each of the highest-performing models above a threshold.

At step 210, the training module 116 organizes the selected neural networks (as determined at step 208) into pairs. In some embodiments, the pairs are determined randomly. In other embodiments, the pairs are determined based on the models' respective performance metrics. For example, the first- and second-highest-performing neural networks may be paired with one another, the third- and fourth-highest-performing models may be paired with one another, and so on. As another example, the highest- and lowest-performing models may be paired with one another, the second-highest- and second-lowest-performing models may be paired with one another, and so on. In some embodiments, step 210 is performed multiple times, which may allow neural networks to "parent" multiple child models with At step 212, the training module 116 forms "child" neural networks. In some embodiments, one child network is formed for each pair of "parent" neural networks determined at step 210. In other embodiments, multiple child networks are formed for each pair of parent neural networks formed at step 210. The child neural networks' weights can be determined using any suitable method. For example, the child neural networks' weights may be determined using arithmetic crossover, where some or all of a child's weights are weighted sums of the parent neural networks' corresponding weights. As another example, the child neural networks' weights may be determined using uniform crossover, where some or all of a child's weights are randomly selected from either parent.

In some embodiments, each of a child neural network's weights is based on one or both of the parent networks' corresponding weights. For example, a weight of a CNN of the child network may be determined based on both (a) a corresponding weight of the first parent network's CNN and (b) a corresponding weight of the second parent network's CNN. Similarly, a weight of an RNN (e.g., LSTM network) of the child network may be determined based on both (a) a corresponding weight of the first parent network's RNN (e.g., LSTM network) and (b) a corresponding weight of the second parent network's RNN (e.g., LSTM network). As discussed, the child network's weights can be determined from the parent networks using any suitable method, such as arithmetic crossover and/or uniform crossover.

In some embodiments, after the child models' weights have been determined, the weights are mutated. This process mimics genetic mutations that occur in biological organisms, further expanding the search space explored by the training module 116. In some embodiments, all weights of a child model are mutated; in other embodiments, only some weights are mutated. In some embodiments, weights are mutated using Gaussian mutation, in which relatively small, normally distributed noise is added to the weights. In some embodiments, the training module 116 may introduce a greater or lesser degree of mutation (e.g., more Gaussian noise) to models based on their parent models' performance (e.g., based on the performance metrics determined at step 206). For example, child models whose parents performed well (e.g., achieved a high performance score as measure on an absolute basis and/or relative to other parent models' performance scores) may be subjected to a lesser degree of mutation compared to child models whose parents performed more poorly.

At step 214, the training module 116 determines whether a convergence criterion has been satisfied. At a high level, the convergence criterion may be a way of determining whether to terminate the genetic algorithm (i.e., evolutionary process). If the convergence criterion is not satisfied, the training module 116 may return to step 208 and iteratively produce additional generations of child models until the convergence criterion is met. Once the convergence criterion is satisfied, the training module 116 may terminate the genetic algorithm and proceed to step 216.

The convergence criterion can be or comprise one or more of the following factors. First, in some embodiments, the convergence criterion is based on model performance. For example, the convergence criterion may be based on a determination that at least one child model exceeds a performance threshold. In these embodiments, the training module 116 may determine performance metrics for each child model (e.g., as discussed with respect to step 206) and compare the performance metrics to the threshold. (In these embodiments, if the convergence criterion is not satisfied, the training module 116 may return to step 208 rather than step 206 since the child models' performance metrics have already been determined.)

Second, in some embodiments, the convergence criterion is based on the number of generations of child models produced by the training module 116. For example, the genetic algorithm may terminate after a predetermined number of generations. In another example, the convergence criterion may be more likely to be satisfied as the number of generations grows, in view of other factors related to the convergence criterion, including those discussed herein.

Third, in some embodiments, the convergence criterion is based on a measure of stability of the child models' performance. For example, if the child models' performance scores are relatively stable across generations, the convergence criterion may be satisfied (or be more likely to be satisfied).

At step 216, the training module 116 selects a best-performing neural network. In some embodiments, the best-performing network is selected from the most recent generation of neural networks. In other embodiments, the best-performing network is selected from more than one generation (e.g., all generations) of neural networks produced via the iterative genetic algorithm. The best-performing network may be determined based on respective networks' performance metrics, as previously described at step 206. For example, the model with the best/highest performance metric may be selected as the best-performing model. In some embodiments, the best-performing model is alternatively or additionally selected based on convergence speed and/or generalization capability.

The training module 116 may provide the best-performing model as an output or export, store the best-performing model in memory, and/or provide an indication to a user (e.g., via a user interface) of the best-performing model.

Steps 202-216 of method 200 may include additional operations that are not described, or not include one or more of the operations described below. The operations of steps 202-216 of method 200 may be performed in any order that facilitates training and/or inference, as described herein. Even though these are shown as separate embodiments, operations from one embodiment may be combined with another. In addition, steps 202-216 are not the only three possible embodiments of method 200. Other variations are contemplated.

FIG. 3 illustrates an example inference process 300 that may be performed by inference module 118 of FIG. 1. Block 302 represents input data. The input data 302 may be data a user desires to classify using a neural network. The input data 302 can comprise any suitable form of data, such as natural language data, time-series data (such as sensor data, stock-price data, or weather data), audio data, video data, and/or medical data (e.g., EHRs). The input data 302 may be preprocessed—e.g., by generating embedding vectors corresponding to the input data 302—prior to being provided as input to a neural network. The input data 302 may comprise a user prompt (e.g., a prompt received from a user device).

The neural network may comprise a CNN 304. The CNN 304 may have any of the properties of the CNN previously discussed with respect with FIG. 2. In some embodiments, different portions, subsets, or modules of the CNN 304 process different embedding vectors concurrently. For example, a first subset of the CNN 304 may process a first subset of embedding vectors generated from the input data 302, and a second subset of the CNN 304 may process a second subset of embedding vectors generated from the input data 302. This may result in a first CNN output and a second CNN output. As shown in FIG. 3, the second CNN output may be provided to, and processed by, an RNN (e.g., an LSTM network 306) of the neural network. The RNN (e.g., LSTM network 306) may, in turn, produce a third output.

In some embodiments, neural network outputs (e.g., the first, second, and/or third outputs) are vectors comprising respective pluralities of probabilities. Each probability may correspond to a classification. To illustrate, the output vector [0.31, 0.41, 0.59] may indicate that the corresponding input data has a 31% chance of corresponding to a first classification, a 41% chance of corresponding to a second classification, and a 59% chance of corresponding to a third classification.

Figure 4:
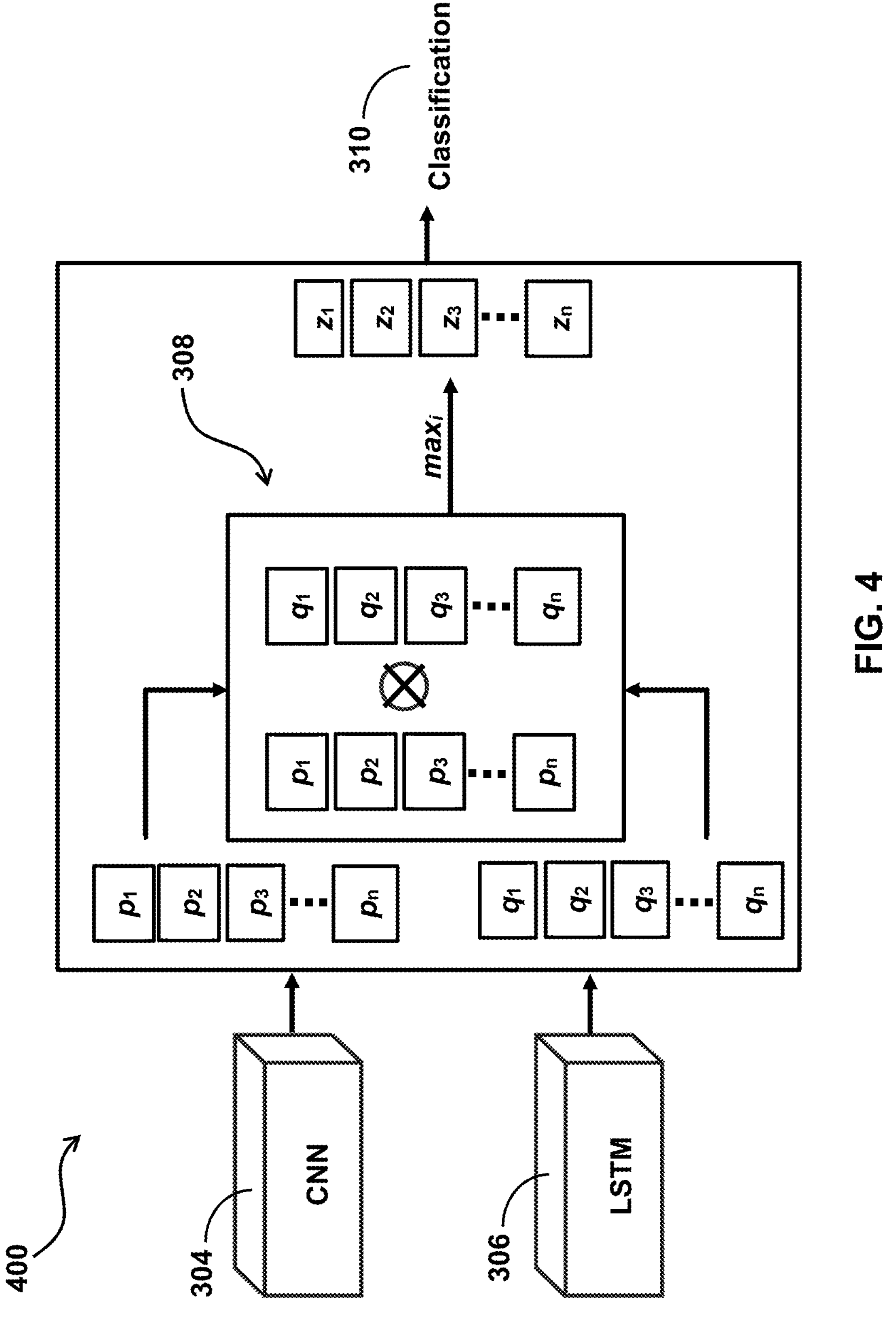
FIG. 4 illustrates an example process of merging neural network outputs.

In some embodiments, the first output (generated by the CNN 304) and the third output (generated by the RNN/LSTM network 306) are combined/merged at block 308 to produce a merged output. An example merge process 400 is shown in more detail in FIG. 4. As shown, each probability $p_1, p_2, \ldots p_n$ of the first output may be merged with a corresponding probability $q_1, q_2, \ldots q_n$ of the third output to produce a merged output vector having probabilities $z_1, z_2, \ldots z_n$. In some embodiments, each probability in the merged output (determined at block 308 in FIGS. 3 and 4) is (or is based on) a maximum of the corresponding probabilities in the first output and third output. In some embodiments, the merged output is computed based on the following equations:

$$P_{CNN}(C=i\,|\,x, W_{2D}, b_{2D}) = \text{softmax}(W_{CNN}x + b_{CNN})$$

$$P_{LSTM}(C=i\,|\,x, W_{LSTM}, b_{LSTM}) = \text{softmax}(W_{LSTM}x + b_{LSTM})$$

$$P_{merged}(C=i\,|\,x) = P_{CNN}(C=i\,|\,x)\cdot P_{LSTM}(C=i\,|\,x)$$

Here, $P_{CNN}$ is the probability predicted by the CNN 304, $P_{LSTM}$ is the probability predicted by the RNN/LSTM network 306, $P_{merged}$ is the merged probability, C is a classification, x corresponds to the input data 302, W corresponds to the weights of the respective model(s), and b represents biases of the respective model(s). This approach, which is not limiting, makes the merged output dependent on, and sensitive to, the outputs of both the CNN 304 and the LSTM 306. That is, if either probability is low, the merged probability will also be low. Similarly, in these embodiments, the merged probability will only be high if both of the unmerged probabilities are also high. Testing has shown that this approach improves classification accuracy, among other benefits.

At block 310, the input data 302 is classified based on the merged output 310. Classification can be performed using any suitable method. In some embodiments, the classification is made according to the highest probability in the merged output vector. This can be accomplished, for example, using an argmax function. To illustrate, if the merged output vector's highest probability is 0.98, and that probability corresponds to a probability that the input is a picture of a cat, the input data 302 may be classified as a picture of a cat.

As discussed, in some embodiments, the training and/or input data 302 comprise EHRs. Neural networks trained on EHRs (e.g., according to process 200) may learn correlations between different health-related variables. For example, in some embodiments, networks are trained on EHRs that comprise information about disease progression (e.g., disease state, timing, symptoms, etc.). Thus, given input data (e.g., one or more EHRs) for a patient that includes a disease diagnosis, neural networks trained in accordance with embodiments herein may make a disease-progression prediction for the patient. The disease-progression prediction may include one or more predictions regarding future disease states, symptoms, and/or the timing thereof.

In some embodiments, networks are trained on EHRs that comprise information about disease risk. That is, networks may learn correlations between certain EHR data and associated diseases (or other diagnoses). To illustrate, a network may learn that a history of tobacco use is correlated with increased risk of cancer. Thus, a trained model, given input data (e.g., one or more EHRs) for a patient, may make a disease-risk prediction for the patient. The disease-risk prediction may include one or more predictions regarding a patient's likelihood of contracting a disease or other diagnosis.

In some embodiments, neural networks trained in accordance with embodiments herein develop patient treatment plans. For example, networks trained on EHRs may learn correlations between diseases or other conditions, treatments (e.g., drugs and/or other treatments), and the associated patient outcome(s) (e.g., recovery time, whether symptoms persisted, whether the patient made a full recovery, etc.). Thus, a trained model, given input data (e.g., one or more EHRs) for a patient, may identify treatment(s) that are most likely to lead to favorable patient outcomes, such as quick recovery from a disease or condition.

Figure 1B:
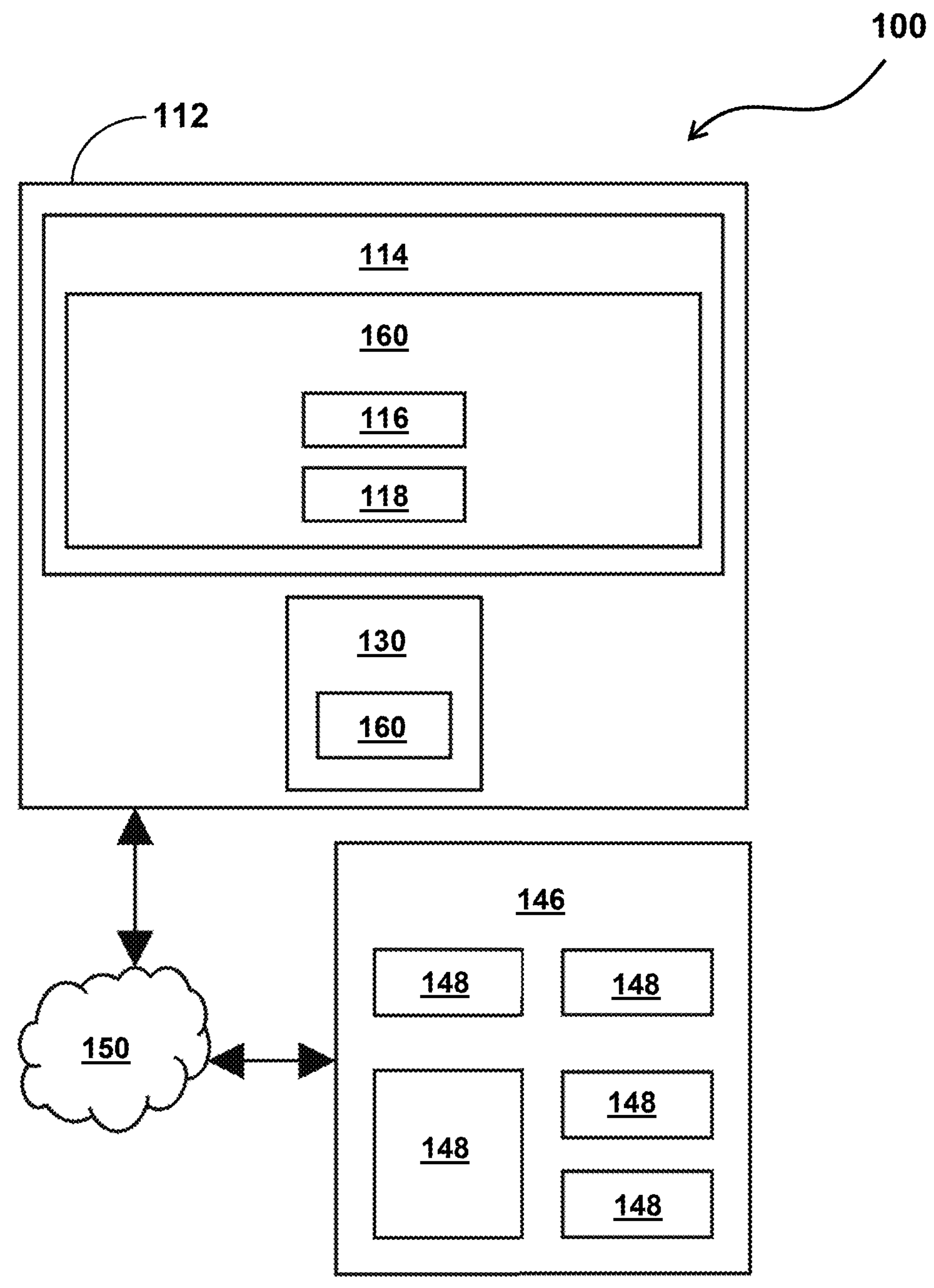
FIG. 1B illustrates a second potential embodiment of the system shown in FIG. 1A.
Figure 1C:
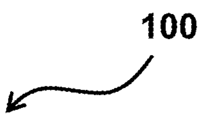
FIG. 1C illustrates a third potential embodiment of the system shown in FIGS. 1A and 1B.
Figure 1C:
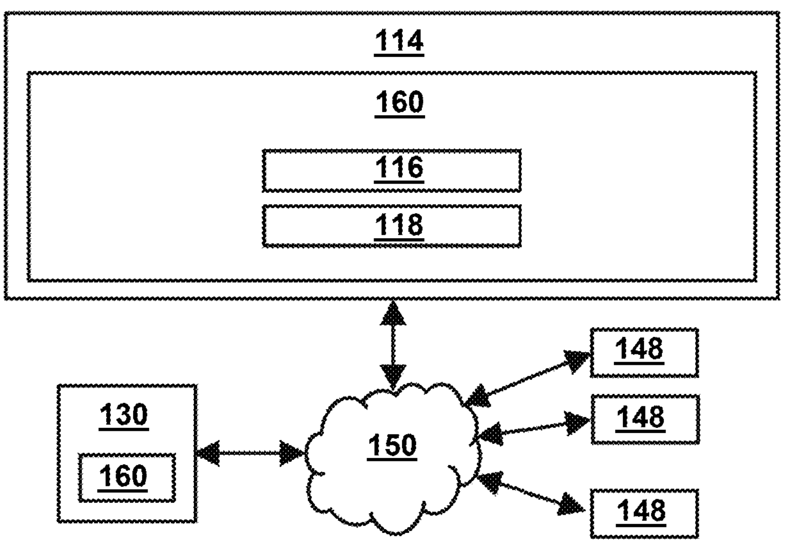
Figure 1D:
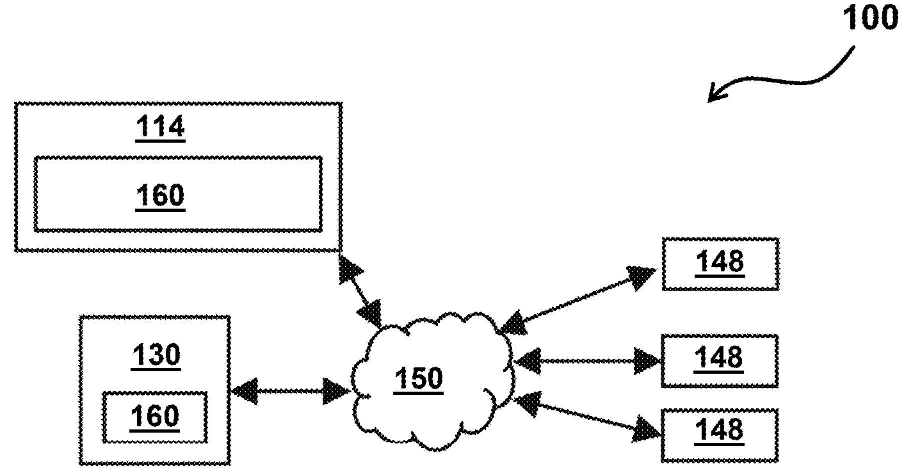
FIG. 1D illustrates a fourth potential embodiment of the system shown in FIG. 1A, FIG. 1B, and FIG. 1C.

Returning to FIG. 1A, system 100 can have many different forms, with or without some or all of the components shown in FIG. 1A, and still be configured to function as described. For example, FIG. 1B, FIG. 1C, and FIG. 1D illustrate examples of alternative potential embodiments of system 100. FIG. 1B illustrates system 100 without API server 126, web server 128, cache server 132, mobile user devices 134 and 136, or desktop user device 138 (e.g., which in this example are their own standalone devices, apart from system 100). FIG. 1C illustrates system 100 with processor 114, instructions 160 (including the different modules 116 and 118), memory 130 (which may or may not be included in the same computing structure as processor 114), and available data sources 148. In this example, the available data sources are each their own separate entity, not necessarily being related to each other. FIG. 1D illustrates system 100 with processor 114, instructions 160 (without being separately divided into the different modules 116 and 118), memory 130 (which again may or may not be included in the same computing structure as processor 114), and available data sources 148. Other embodiments with different arrangements of components are contemplated.

In FIGS. 1A-1D, the different components of system 100 are illustrated communicating via network 150. This is not intended to be limiting. As described herein, different components of system 100 communicate via network 150 (as shown), via wired connections, or via other wired or wireless connections. The illustrated components communicate directly with each other (e.g., via network 150 or a wired connection), or indirectly via other components of system 100.

Returning to FIGS. 1A (and 1B, 1C, or 1D), it should be noted that in some embodiments, computing engine 112 is configured such that in the above-mentioned operations of processor 114, and input from users or sources of information inside or outside system 100, are processed by processor 114 through a variety of formats, including clicks, touches, uploads, downloads, etc. The illustrated components (e.g., processor 114, API server 126, web server 128, memory 130, and cache server 132) of computing engine 112 are depicted as discrete functional blocks, but embodiments are not limited to systems in which the functionality described herein is organized as illustrated by FIG. 1A. In some embodiments, the functionality provided by each of the components of computing engine 112 is provided by software or hardware modules that are differently organized than is presently depicted, for example such software or hardware is intermingled, broken up, distributed (e.g., within a data center or geographically), or otherwise differently organized. In some embodiments, the functionality described is provided by one or more processors of one or more computers executing code stored on a tangible, non-transitory, machine readable medium.

In some embodiments, computing engine 112 is provided with or within one or more portions of a multimodal model, or multiple multimodal models that include one or more neural networks. In some embodiments, these models, or portions thereof, are generated, executed, or otherwise utilized by computing engine 112 or processor 114 (or one or more of the components of processor 114) as shown in FIGS. 1A, 1B, and 1C, and described above.

In some embodiments, a multimodal model comprises a large language model (LLM), a generative model, or other models. In some embodiments, the multimodal model comprises one or more individual algorithms (e.g., that form a LLM, a generative model, a transformer, a neural network, an adapter, etc.). In some embodiments, an algorithm is a machine learning algorithm. In some embodiments, the machine learning algorithm is or includes a neural network, classification tree, decision tree, support vector machine, or other model that is trained and configured to output a response to input query. As an example, neural networks are based on a large collection of neural units (or artificial neurons). Neural networks loosely mimic the manner in which a biological brain works (e.g., via large clusters of biological neurons connected by axons). Each neural unit of a neural network is simulated as being connected with many other neural units of the neural network. Such connections can be enforcing or inhibitory in their effect on the activation state of connected neural units. In some embodiments, each individual neural unit has a summation function which combines the values of all its inputs together. In some embodiments, each connection (or the neural unit itself) has a threshold function such that the signal must surpass the threshold before it is allowed to propagate to other neural units. These neural network systems are self-learning and trained, rather than explicitly programmed, and can perform significantly better in certain areas of problem solving, as compared to traditional computer programs. In some embodiments, neural networks include multiple layers (e.g., where a signal path traverses from front layers to back layers). In some embodiments, back propagation techniques are utilized by the neural networks, where forward stimulation is used to reset weights on the "front" neural units. In some embodiments, stimulation and inhibition for neural networks is more free flowing, with connections interacting in a more chaotic and complex fashion.

Data is extracted by processor 114 or other components of system 100 from memory 130 or external resources 146, or other sources inside or outside system 100 in a secure and encrypted fashion. Data extraction by processor 114 is configured to be sufficient for system 100 to function as described herein, without compromising privacy or other requirements associated with a data source.

It should be appreciated that although modules 116 and 118 are illustrated in FIGS. 1A (and 1B and 1C) as being co-located, one or more of modules 116 and 118 may be located remotely from the other modules. The description of the functionality provided by the different modules 116 and 118 described below is for illustrative purposes, and is not intended to be limiting, as any of the modules 116 and 118 may provide more or less functionality than is described, which is not to imply that other descriptions are limiting. For example, one or more of modules 116 and 118 may be eliminated, and some or all of its functionality may be provided by others of the modules 116 and 118 again which is not to imply that other descriptions are limiting. As another example, processor 114 may be configured to control one or more additional modules that perform some or all of the functionality attributed to one of the modules 116 and 118.

Modules 116 and 118 are program instructions that are executable by a processor 114 to implement one or more embodiments of the present techniques. In some embodiments, program instructions include a computer program (which in certain forms is known as a program, software, software application, script, or code). A computer program is written in a programming language, including compiled or interpreted languages, or declarative or procedural languages. In some embodiments, a computer program includes a unit suitable for use in a computing environment, including as a stand-alone program, a module, a component, or a subroutine. In some embodiments, a computer program corresponds to a file in a file system. A program is stored in a portion of a file that holds other programs or data (e.g., one or more scripts stored in a markup language document), in a single file dedicated to the program in question, or in multiple coordinated files (e.g., files that store one or more modules, sub programs, or portions of code). In some embodiments, a computer program is deployed to be executed on one or more computer processors located locally at one site or distributed across multiple remote sites and interconnected by a communication network, for example.

Cache server 132 expedites access to relevant data by storing likely relevant data in relatively high-speed memory, for example, in random-access memory or a solid-state drive (e.g., formed by at least a portion of memory 130). Web server 128 serves webpages having graphical user interfaces that display one or more views that facilitate receiving entry or selection of input from a user (e.g., including a query or command that system 100 perform a certain task, providing context, etc.), or other views. API server 126 serves data to various applications that process data related to user requested tasks, or other data. The operation of these components (API server 126, web server 128, and memory 130) is coordinated by processor 114, which bidirectionally communicates with each of these components or directs the components to communicate with one another. Communication occurs by transmitting data between separate computing devices (e.g., via transmission control protocol/internet protocol (TCP/IP) communication over a network), by transmitting data between separate applications or processes on one computing device; or by passing values to and from functions, modules, or objects within an application or process, e.g., by reference or by value.

API server 126 is configured to communicate user input query text commands, input images, and/or other information via a protocol, such as a representational-state-transfer (REST)-based API protocol over hypertext transfer protocol (HTTP) or other protocols. API requests identify which output data is to be determined, displayed, linked, modified, added, or retrieved by specifying criteria for identifying query intent tasks, such as queries for retrieving or processing information about a particular subject. In some embodiments, API server 126 communicates with native application 140 of the mobile user device 134, native application 145 of desktop user device 138, or other components of system 100.

Web server 128 is configured to display, link, modify, add, or retrieve portions or all of an output associated with a user input query, or other information encoded in a webpage (e.g. a collection of resources to be rendered by the browser and associated plug-ins, including execution of scripts, such as JavaScript™, invoked by the webpage). In some embodiments, the graphical user interface presented by the webpage includes inputs by which the user enters or selects data, such as clickable or touchable display regions or display regions for text input. For example, context information such as screen shots, documents, etc., may be uploaded, in combination with one or more entered text commands. Such inputs prompt the browser to request additional data from web server 128 or transmit data to web server 128, and web server 128 responds to such requests by obtaining the requested data and returning it to the user device or acting upon the transmitted data (e.g., storing posted data or executing posted commands). In some embodiments, the requests are for a new webpage or for data upon which client-side scripts will base changes in the webpage, such as XMLHttpRequest requests for data in a serialized format, e.g. JavaScript™ object notation (JSON) or extensible markup language (XML). Web server 128 communicates with web browsers, such as web browser 142 or 144 executed by user devices 136 or 138. In some embodiments, the webpage is modified by web server 128 based on the type of user device, e.g., with a mobile webpage having fewer and smaller images and a narrower width being presented to the mobile user device 136, and a larger, more content rich webpage being presented to the desktop user device 138. In some embodiments, an identifier of the type of user device, either mobile or non-mobile, for example, is encoded in the request for the webpage by the web browser (e.g., as a user agent type in an HTTP header associated with a GET request), and web server 128 selects the appropriate interface based on this embedded identifier, thereby providing an interface appropriately configured for the specific user device in use.

Web browsers 142 and 144 are configured to receive a website from computing engine 112 having data related to instructions (for example, instructions expressed in JavaScript™) that when executed by the browser (which is executed by the processor) cause mobile user devices 134 or 136, or desktop user device 138, to communicate with computing engine 112 and facilitate user interaction with data from computing engine 112. Native applications 140 and 145, and web browsers 142 and 144, upon rendering a webpage or a graphical user interface from computing engine 112, may generally be referred to as client applications of computing engine 112, which in some embodiments may be referred to as a server. Embodiments, however, are not limited to client/server architectures, and computing engine 112, as illustrated, may include a variety of components other than those functioning primarily as a server. Three user devices are shown, but embodiments are expected to interface with substantially more, with more than 100 concurrent sessions and serving more than 1 million users distributed over a relatively large geographic area, such as a state, the entire United States, and/or multiple countries across the world.

Though not illustrated in FIG. 1A (or 1B, 1C, or 1D), computing engine 112, in some embodiments, includes multiple processors 114, an input/output I/O device interface, and a network interface via an input/output (I/O) interface. In some embodiments, multiple processors are employed to provide for parallel or sequential execution of one or more portions of the techniques described herein. The I/O device interface provides an interface for connection of one or more I/O devices to computing engine 112. I/O devices include devices that receive input (e.g., from a user) or output information (e.g., to a user). I/O devices include, for example, graphical user interfaces presented on displays (e.g., a touchscreen or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices are connected to computing engine through a wired or wireless connection. I/O devices are connected to computing engine 112 from a remote location. I/O devices located on a remote computer system, for example, are connected to computing engine 112 via network 150 and the network interface.

The network interface includes a network adapter that provides for connection of computing engine 112 to network 150. The network interface facilitates data exchange between computing engine 112 and other devices connected to network 150. The network interface supports wired or wireless communication. In some embodiments, network 150 includes an electronic communication network, such as the Internet, a local area network (LAN), a wide area network (WAN), a cellular communications network, or the like.

The I/O interface is configured to coordinate I/O traffic between processors, memory 130, the network interface, I/O devices, or other peripheral devices. The I/O interface performs protocol, timing, or other data transformations to convert data signals from one component (e.g., memory 130) into a format suitable for use by another component (e.g., processor(s) 114). In some embodiments, the I/O interface includes support for devices attached through various types of peripheral buses, such as a variant of the Peripheral Component Interconnect (PCI) bus standard or the Universal Serial Bus (USB) standard.

Embodiments of the techniques described herein may be implemented using a single instance of computing engine 112 or multiple computer systems configured to host different portions or instances of embodiments. Multiple computer systems may provide for parallel or sequential processing/execution of one or more portions of the techniques described herein.

While various items are illustrated as being stored in memory, these items or portions of them may be transferred between memory and other storage devices for purposes of memory management and data integrity. Alternatively, in other embodiments some or all of the software components executes in memory on another device and communicates with the illustrated computer system via inter-computer communication. In some embodiments, some or all of the system components or data structures are stored (e.g., as instructions or structured data) on a computer-accessible medium or a portable article to be read by an appropriate drive, various examples of which are described above. In some embodiments, instructions stored on a computer-accessible medium separate from computing engine 112 are transmitted to computing engine 112 via transmission media or signals such as electrical, electromagnetic, or digital signals, conveyed via a communication medium such as a network or a wireless link. Various embodiments include receiving, sending, or storing instructions or data implemented in accordance with the foregoing description upon a computer-accessible medium. Accordingly, the present techniques may be practiced with other computer system configurations.

To mitigate the problems described herein, the inventor had to both invent solutions and, in some cases just as importantly, recognize problems overlooked (or not yet foreseen) by others in the field of neural networks, and other fields. The inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium". In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several embodiments. Rather than separating those embodiments into multiple isolated patent applications, applicants have grouped these embodiments into a single document because their related subject matter lends itself to economies in the application process. But the distinct advantages and aspects of these embodiments should not be conflated. In some cases, embodiments address all of the deficiencies noted herein, but it should be understood that the embodiments are independently useful, and some embodiments address only a subset of such problems or offer other, unmentioned benefits that will be apparent to those of skill in the art reviewing the present disclosure. Due to cost constraints, some disclosed embodiments are not presently claimed and may be claimed in later filings, such as continuation applications or by amending the present claims. Similarly, due to space constraints, neither the Abstract nor the Summary sections of the present document should be taken as containing a comprehensive listing of all such embodiments or all aspects of such embodiments.

It should be understood that the description and the drawings are not intended to limit an embodiment to the particular form disclosed, but to the contrary, the intention is to cover all modifications, equivalents, and alternatives falling within the spirit and scope of the present embodiments as defined by the appended claims. Further modifications and alternative embodiments will be apparent to those skilled in the art in view of this description. Accordingly, this description and the drawings are to be construed as illustrative only and are for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features may be utilized independently, all as would be apparent to one skilled in the art after having the benefit of this description. Changes may be made in the elements described without departing from the spirit and scope of the embodiments as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

The present techniques will be better understood with reference to the following enumerated embodiments:

A method comprising: initializing a first plurality of neural networks; determining performance metrics, each of the performance metrics corresponding to a respective neural network of the first plurality of neural networks, wherein each of the performance metrics is based on accuracy of the respective neural network in evaluating a training dataset; selecting a subset of the first plurality of neural networks based on the performance metrics; selecting a first neural network from the subset and a second neural network from the subset, wherein the first neural network comprises a first convolutional neural network (CNN) and a first recurrent neural network (RNN), and wherein the second neural network comprises a second CNN and a second RNN; and forming a third neural network, wherein forming the third neural network comprises selecting weights of the first neural network, selecting weights of the second neural network, and forming the third neural network at least in part from the selected weights of the first and second neural networks.

The method of any of the previous embodiments, wherein forming the third neural network at least in part from the selected weights of the first and second neural networks comprises: forming a third CNN of the third neural network from weights of the first CNN and weights of the second CNN; and forming a third RNN of the third neural network from weights of the first RNN and weights of the second RNN.

The method of any of the previous embodiments, further comprising: providing, to the third neural network, a plurality of embedding vectors generated from input data; processing, by the third CNN, a first subset of the embedding vectors, thereby producing a first CNN output; processing, by the third CNN, a second subset of the embedding vectors, thereby producing a second CNN output; processing, by the third RNN, the second CNN output, thereby producing an RNN output; combining the first CNN output with the RNN output, thereby producing a merged output; and classifying the input data based on the merged output.

The method of any of the previous embodiments, wherein the first RNN comprises a first long short-term memory (LSTM) network, the second RNN comprises a second LSTM network, and the third RNN comprises a third LSTM network.

The method of any of the previous embodiments, wherein the input data comprises an electronic health record (EHR).

The method of any of the previous embodiments, wherein classifying the input data comprises generating at least one of the following: a patient treatment plan, a disease-progression prediction, or a disease-risk prediction.

The method of any of the previous embodiments, further comprising: determining that a convergence criterion has been satisfied based at least in part on an accuracy of the classification of the input data.

The method of any of the previous embodiments, further comprising applying random variations to weights of the third neural network.

The method of any of the previous embodiments, wherein the training dataset comprises artificial electronic health records (EHRs) generated by combining elements of patient EHRs.

The method of any of the previous embodiments, wherein the first RNN comprises a first LSTM network, the second RNN comprises a second LSTM network.

The method of any of the previous embodiments, wherein the third neural network comprises a third CNN and a third LSTM network.

The method of any of the previous embodiments, wherein the third neural network is configured to provide an output of the third CNN to the third LSTM network.

The method of any of the previous embodiments, wherein each of the first CNN, the second CNN, and the third CNN is a respective two-dimensional CNN.

The method of any of the previous embodiments, wherein the first neural network and the second neural network are randomly selected from the subset.

A system comprising: a processor; and memory storing instructions that, when executed by the processor, cause the processor to: initialize a first plurality of neural networks; determine performance metrics, each of the performance metrics corresponding to a respective neural network of the first plurality of neural networks, wherein each of the performance metrics is based on accuracy of the respective neural network in evaluating a training dataset; select a subset of the first plurality of neural networks based on the performance metrics; select a first neural network from the subset and a second neural network from the subset, wherein the first neural network comprises a first convolutional neural network (CNN) and a first recurrent neural network (RNN), and wherein the second neural network comprises a second CNN and a second RNN; and form a third neural network, wherein forming the third neural network comprises selecting weights of the first neural network, selecting weights of the second neural network, and forming the third neural network at least in part from the selected weights of the first and second neural networks.

The system of any of the previous embodiments, wherein forming the third neural network at least in part from the selected weights of the first and second neural networks comprises: forming a third CNN of the third neural network from weights of the first CNN and weights of the second CNN; and forming a third RNN of the third neural network from weights of the first RNN and weights of the second RNN.

The system of any of the previous embodiments, wherein the instructions further cause the processor to: provide, to the third neural network, a plurality of embedding vectors generated from input data; process, by the third CNN, a first subset of the embedding vectors, thereby producing a first CNN output; process, by the third CNN, a second subset of the embedding vectors, thereby producing a second CNN output; process, by the third RNN, the second CNN output, thereby producing an RNN output; combine the first CNN output with the RNN output, thereby producing a merged output; and classify the input data based on the merged output.

The system of any of the previous embodiments, wherein the first RNN comprises a first long short-term memory (LSTM) network, the second RNN comprises a second LSTM network, and the third RNN comprises a third LSTM network.

The system of any of the previous embodiments, wherein the input data comprises an electronic health record (EHR).

The system of any of the previous embodiments, wherein classifying the input data comprises generating at least one of the following: a patient treatment plan, a disease-progression prediction, or a disease-risk prediction.

The system of any of the previous embodiments, wherein the instructions further cause the processor to: determine that a convergence criterion has been satisfied based at least in part on an accuracy of the classification of the input data.

The system of any of the previous embodiments, wherein the instructions further cause the processor to apply random variations to weights of the third neural network.

The system of any of the previous embodiments, wherein the training dataset comprises artificial electronic health records (EHRs) generated by combining elements of patient EHRs.

The system of any of the previous embodiments, wherein the first RNN comprises a first LSTM network, the second RNN comprises a second LSTM network.

The system of any of the previous embodiments, wherein the third neural network comprises a third CNN and a third LSTM network.

The system of any of the previous embodiments, wherein the third neural network is configured to provide an output of the third CNN to the third LSTM network.

The system of any of the previous embodiments, wherein each of the first CNN, the second CNN, and the third CNN is a respective two-dimensional CNN.

The system of any of the previous embodiments, wherein the first neural network and the second neural network are randomly selected from the subset.

A non-transitory computer readable medium having instructions thereon, the instructions, when executed by a computer, causing the computer to perform operations comprising: initializing a first plurality of neural networks; determining performance metrics, each of the performance metrics corresponding to a respective neural network of the first plurality of neural networks, wherein each of the performance metrics is based on accuracy of the respective neural network in evaluating a training dataset; selecting a subset of the first plurality of neural networks based on the performance metrics; selecting a first neural network from the subset and a second neural network from the subset, wherein the first neural network comprises a first convolutional neural network (CNN) and a first recurrent neural network (RNN), and wherein the second neural network comprises a second CNN and a second RNN; and forming a third neural network, wherein forming the third neural network comprises selecting weights of the first neural network, selecting weights of the second neural network, and forming the third neural network at least in part from the selected weights of the first and second neural networks.

The medium of any of the previous embodiments, wherein forming the third neural network at least in part from the selected weights of the first and second neural networks comprises: forming a third CNN of the third neural network from weights of the first CNN and weights of the second CNN; and forming a third RNN of the third neural network from weights of the first RNN and weights of the second RNN.

The medium of any of the previous embodiments, wherein the instructions cause the computer to perform operations further comprising: providing, to the third neural network, a plurality of embedding vectors generated from input data; processing, by the third CNN, a first subset of the embedding vectors, thereby producing a first CNN output; processing, by the third CNN, a second subset of the embedding vectors, thereby producing a second CNN output; processing, by the third RNN, the second CNN output, thereby producing an RNN output; combining the first CNN output with the RNN output, thereby producing a merged output; and classifying the input data based on the merged output.

The medium of any of the previous embodiments, wherein the first RNN comprises a first long short-term memory (LSTM) network, the second RNN comprises a second LSTM network, and the third RNN comprises a third LSTM network.

The medium of any of the previous embodiments, wherein the input data comprises an electronic health record (EHR).

The medium of any of the previous embodiments, wherein classifying the input data comprises generating at least one of the following: a patient treatment plan, a disease-progression prediction, or a disease-risk prediction.

The medium of any of the previous embodiments, wherein the instructions cause the computer to perform operations further comprising: determining that a convergence criterion has been satisfied based at least in part on an accuracy of the classification of the input data.

The medium of any of the previous embodiments, wherein the instructions cause the computer to perform operations further comprising applying random variations to weights of the third neural network.

The medium of any of the previous embodiments, wherein the training dataset comprises artificial electronic health records (EHRs) generated by combining elements of patient EHRs.

The medium of any of the previous embodiments, wherein the first RNN comprises a first LSTM network, the second RNN comprises a second LSTM network.

The medium of any of the previous embodiments, wherein the third neural network comprises a third CNN and a third LSTM network.

The medium of any of the previous embodiments, wherein the third neural network is configured to provide an output of the third CNN to the third LSTM network.

The medium of any of the previous embodiments, wherein each of the first CNN, the second CNN, and the third CNN is a respective two-dimensional CNN.

The medium of any of the previous embodiments, wherein the first neural network and the second neural network are randomly selected from the subset.

The invention claimed is:

1. A method comprising:

initializing a first plurality of neural networks;

training the first plurality of neural networks on training data, wherein the training data comprises artificial first electronic health records (EHRs) generated by combining elements of patient EHRs, and wherein the first EHRs comprise patient demographics, medical diagnoses, medication information, laboratory test results, and medical imaging;

determining performance metrics, each of the performance metrics corresponding to a respective neural network of the first plurality of neural networks, wherein each of the performance metrics is based on accuracy of the respective neural network;

selecting a subset of the first plurality of neural networks based on the performance metrics;

selecting a first neural network from the subset and a second neural network from the subset, wherein the first neural network comprises a first convolutional neural network (CNN) and a first long short-term memory (LSTM) network, and wherein the second neural network comprises a second CNN and a second LSTM network;

forming a third neural network, wherein forming the third neural network comprises (a) selecting weights of the first CNN, selecting weights of the second CNN, and forming a third CNN of the third neural network at least in part from the selected weights of the first CNN and the second CNN and (b) selecting weights of the first LSTM network, selecting weights of the second LSTM network, and forming a third LSTM network of the third neural network at least in part from the selected weights of the first LSTM network and the second LSTM network;

providing, to the third neural network, a plurality of embedding vectors generated from second EHRs;

processing, by the third CNN, a first subset of the embedding vectors, thereby producing a first output of the third CNN, wherein the third LSTM network does not process the first output of the third CNN;

processing, by the third CNN, a second subset of the embedding vectors, thereby producing a second output of the third CNN;

processing, by the third LSTM network, the second output of the third CNN, thereby producing an output of the third LSTM network;

combining the first output of the third CNN with the output of the third LSTM network, thereby producing a merged output;

classifying the second EHRs based on the merged output;

receiving a medical diagnosis for a patient, the patient corresponding to the second EHRs; and generating a disease-progression prediction for the patient based on the medical diagnosis and the classification of the second EHRs.

2. The method of claim 1, further comprising:

determining that a convergence criterion has been satisfied based at least in part on an accuracy of the classification of the second EHRs.

3. The method of claim 1, further comprising applying random variations to weights of the third neural network.

4. The method of claim 1, wherein each of the first CNN, the second CNN, and the third CNN is a respective two-dimensional CNN.

5. The method of claim 1, wherein the first neural network and the second neural network are randomly selected from the subset.

6. A system comprising:
a processor; and
memory storing instructions that, when executed by the processor, cause the processor to:
initialize a first plurality of neural networks;
train the first plurality of neural networks on training data,
wherein the training data comprises artificial first electronic health records (EHRs) generated by combining elements of patient EHRs, and
wherein the first EHRs comprise patient demographics, medical diagnoses, medication information, laboratory test results, and medical imaging;
determine performance metrics, each of the performance metrics corresponding to a respective neural network of the first plurality of neural networks,
wherein each of the performance metrics is based on accuracy of the respective neural network;
select a subset of the first plurality of neural networks based on the performance metrics;
select a first neural network from the subset and a second neural network from the subset,
wherein the first neural network comprises a first convolutional neural network (CNN) and a first long short-term memory (LSTM) network, and
wherein the second neural network comprises a second CNN and a second LSTM network;
form a third neural network, wherein forming the third neural network comprises (a) selecting weights of the first CNN, selecting weights of the second CNN, and forming a third CNN of the third neural network at least in part from the selected weights of the first CNN and the second CNN and (b) selecting weights of the first LSTM network, selecting weights of the second LSTM network, and forming a third LSTM network of the third neural network at least in part from the selected weights of the first LSTM network and the second LSTM network;
provide, to the third neural network, a plurality of embedding vectors generated from second EHRs;
process, by the third CNN, a first subset of the embedding vectors, thereby producing a first output of the third CNN, wherein the third LSTM network does not process the first output of the third CNN;
process, by the third CNN, a second subset of the embedding vectors, thereby producing a second output of the third CNN;
process, by the third LSTM network, the second output of the third CNN, thereby producing an output of the third LSTM network;
combine the first output of the third CNN with the output of the third LSTM network, thereby producing a merged output;
classify the second EHRs based on the merged output;
receive a medical diagnosis for a patient, the patient corresponding to the second EHRs; and
generate a disease-progression prediction for the patient based on the medical diagnosis and the classification of the second EHRs.

7. A non-transitory computer readable medium having instructions thereon, the instructions, when executed by a computer, causing the computer to perform operations comprising:
initializing a first plurality of neural networks;
training the first plurality of neural networks on training data,
wherein the training data comprises artificial first electronic health records (EHRs) generated by combining elements of patient EHRs, and
wherein the first EHRs comprise patient demographics, medical diagnoses, medication information, laboratory test results, and medical imaging;
determining performance metrics, each of the performance metrics corresponding to a respective neural network of the first plurality of neural networks,
wherein each of the performance metrics is based on accuracy of the respective neural network;
selecting a subset of the first plurality of neural networks based on the performance metrics;
selecting a first neural network from the subset and a second neural network from the subset,
wherein the first neural network comprises a first convolutional neural network (CNN) and a first long short-term memory (LSTM) network, and
wherein the second neural network comprises a second CNN and a second LSTM network;
forming a third neural network, wherein forming the third neural network comprises (a) selecting weights of the first CNN, selecting weights of the second CNN, and forming a third CNN of the third neural network at least in part from the selected weights of the first CNN and the second CNN and (b) selecting weights of the first LSTM network, selecting weights of the second LSTM network, and forming a third LSTM network of the third neural network at least in part from the selected weights of the first LSTM network and the second LSTM network;
providing, to the third neural network, a plurality of embedding vectors generated from second EHRs;
processing, by the third CNN, a first subset of the embedding vectors, thereby producing a first output of the third CNN, wherein the third LSTM network does not process the first output of the third CNN;
processing, by the third CNN, a second subset of the embedding vectors, thereby producing a second output of the third CNN;
processing, by the third LSTM network, the second output of the third CNN, thereby producing an output of the third LSTM network;
combining the first output of the third CNN with the output of the third LSTM network, thereby producing a merged output;
classifying the second EHRs based on the merged output;
receiving a medical diagnosis for a patient, the patient corresponding to the second EHRs; and
generating a disease-progression prediction for the patient based on the medical diagnosis and the classification of the second EHRs.

8. The method of claim 1, wherein the merged output is based on a maximum of the first output of the third CNN and the output of the third LSTM network.

9. The system of claim 6, wherein the merged output is based on a maximum of the first output of the third CNN and the output of the third LSTM network.

10. The medium of claim 7, wherein the merged output is based on a maximum of the first output of the third CNN and the output of the third LSTM network.

* * * * *